United States Patent

Tanaka et al.

Patent Number: 5,395,309
Date of Patent: Mar. 7, 1995

[54] NASAL PACK APPLICATOR

[75] Inventors: Kazuna Tanaka, Cos Cob; Jeffrey Kapec, Westport, both of Conn.

[73] Assignee: Merocel Corporation, Mystic, Conn.

[21] Appl. No.: 133,339

[22] Filed: Oct. 8, 1993

[51] Int. Cl.⁶ .............................................. A61F 13/20
[52] U.S. Cl. ......................................... 604/18; 604/11; 604/12; 604/13; 604/15; 604/2; 604/904
[58] Field of Search ........................................ 604/1–2, 604/11–18, 904

[56]  References Cited

U.S. PATENT DOCUMENTS

| | | |
|---|---|---|
| 604,393 | 5/1898 | Hooker . |
| 702,570 | 6/1902 | Lohlein . |
| 702,997 | 6/1902 | Pugh . |
| 3,015,332 | 1/1962 | Brecht . |
| 3,068,867 | 12/1962 | Bletzinger et al. . |
| 3,101,713 | 8/1963 | Sargent . |
| 3,103,929 | 9/1963 | Brecht . |
| 3,196,873 | 7/1965 | Bletzinger et al. ............ 604/15 |
| 3,433,225 | 3/1969 | Voss et al. . |
| 3,643,661 | 2/1972 | Crockford ..................... 604/15 |
| 3,674,026 | 7/1972 | Werner et al. . |
| 3,765,416 | 10/1973 | Werner et al. . |
| 3,911,922 | 10/1975 | Kliger . |
| 3,971,378 | 7/1976 | Krantz . |
| 4,020,844 | 5/1977 | Vickery . |
| 4,098,720 | 7/1978 | Hwa . |
| 4,291,696 | 9/1981 | Ring . |
| 4,411,647 | 10/1983 | Sakurai et al. . |
| 4,457,756 | 7/1984 | Kern et al. . |
| 4,479,791 | 10/1984 | Sprague . |
| 4,536,178 | 8/1985 | Lichstein et al. ............. 604/15 |
| 4,573,963 | 3/1986 | Sheldon ......................... 604/11 |
| 4,676,773 | 6/1987 | Sheldon . |
| 4,895,559 | 1/1990 | Shippert . |

FOREIGN PATENT DOCUMENTS

| | | | |
|---|---|---|---|
| 0532745 | 1/1941 | United Kingdom | 604/904 |
| 8706143 | 10/1987 | WIPO | 604/2 |

*Primary Examiner*—Randall L. Green
*Assistant Examiner*—P. Zuttarelli
*Attorney, Agent, or Firm*—Gipple & Hale

[57]  ABSTRACT

A nasal pack inserter apparatus having a barrel member with a throughgoing lumen providing an inlet and an outlet for a plunger reciprocally mounted therein. The barrel member defines rib means projecting into the throughgoing lumen defining a track for the plunger which is configured to fit in the track when inserted into the lumen. The plunger member has a thumb piece on one end and a pusher tip on the other end to transport a nasal pack provided with a withdrawal thread through the lumen into a nasal cavity. The withdrawal thread of the nasal pack is positioned within a channel formed in the plunger body to prevent fouling of the same within the barrel lumen.

16 Claims, 3 Drawing Sheets

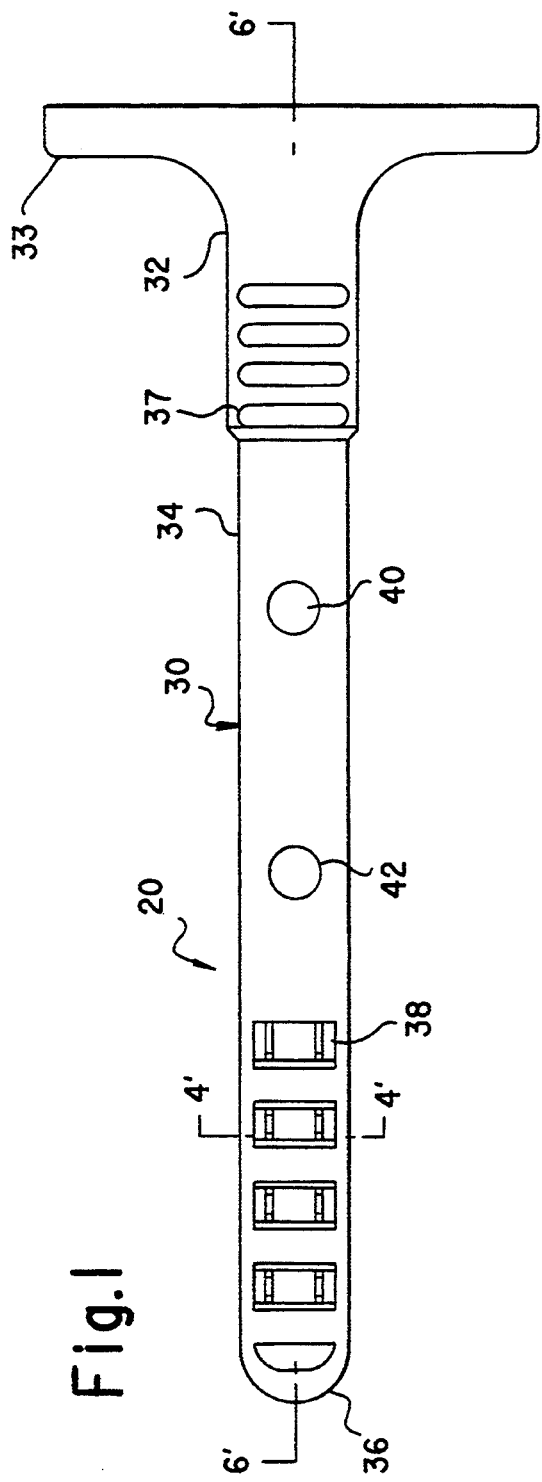

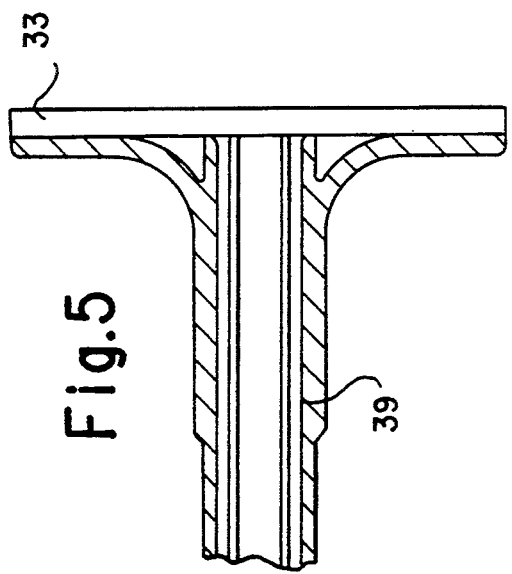
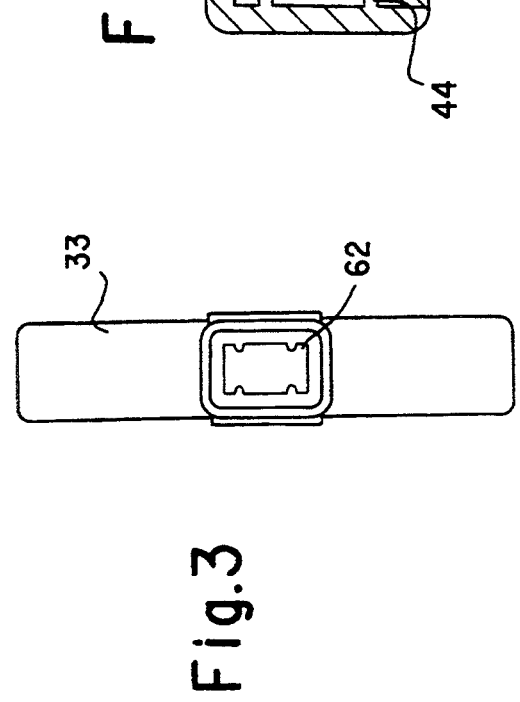
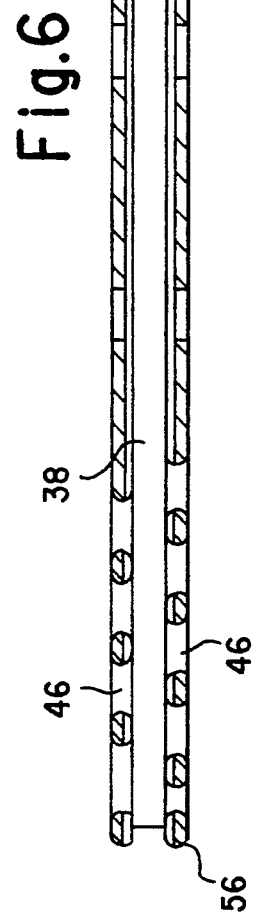
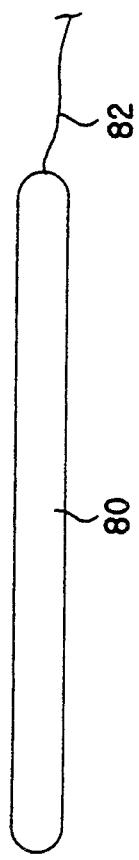

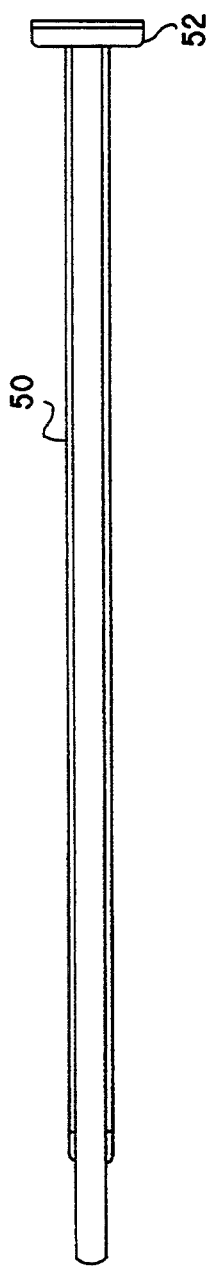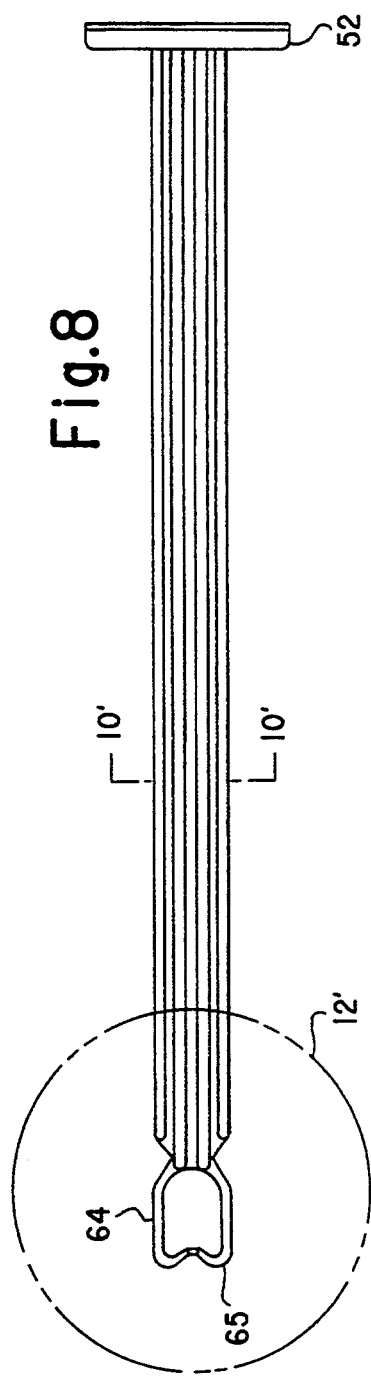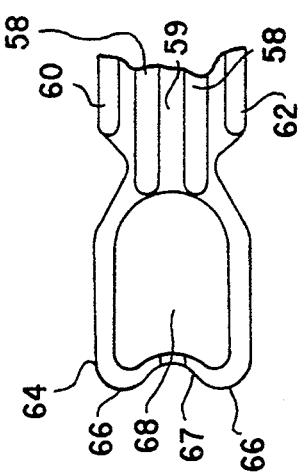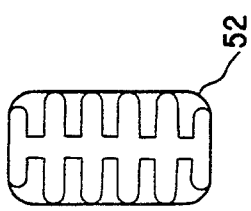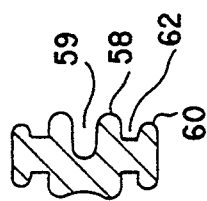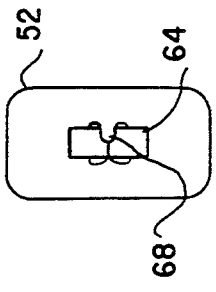

NASAL PACK APPLICATOR

BACKGROUND OF THE INVENTION

1. Field of Invention

The present invention generally relates to the treatment of nasal hemorrhages and more particularly to a nasal pack applicator which provides for the insertion of a preformed nasal pack into a nasal cavity.

2. Background of the Invention

Generally nasal hemorrhaging from surgery is treated by packing the nasal cavity with an absorbent material. A number of different types of absorbent materials have been used such as gauze, sponge and various cellulosic fibers. Nasal packs formed of a dry polyvinyl acetal sponge material, which expand when hydrated, have been marketed by Merocel Inc. for more than 10 years and are well known commercially in the medical community.

There are a wide number of methods and apparatus used for inserting a nasal pack or tampon into a nasal or other cavity.

U. S. Pat. No. 4,030,504 utilizes an expandable absorbent material nasal pack contoured to conform to the nasal cavity. This pack is inserted by hand into the nasal cavity of the patient.

While some surgeons typically trim the expandable absorbent material to the appropriate size and manually insert the device into a patient's nasal as has been previously noted, a number of insertion devices have been on the market which utilize a plunger-type device to insert an absorbent pack into a patient.

One such patent is U.S. Pat. No. 3,068,867 which shows the use of a cellulosic rectangular shaped tampon which is compressed to one form or cross section when dry and then subjected to fluids, at which time it expands to a second size. The tampon is placed in an applicator or barrel with the end of the plunger contacting the end of the tampon which is the same cross section throughout its length as that of the barrel. The tampon used in the device has a string attached to its distal end which can extend back through the interior of the plunger if the plunger is hollow or back past the exterior of the plunger if the plunger is solid.

A substantially identical device is shown in U.S. Pat. No. 4,895,559 which shows a nasal pack syringe having a barrel and a plunger made from plastic with the end of the plunger engaging the nasal pack being formed with a pair of prongs which extend laterally outward from the barrel shaft so that they are slightly wider than the shaft. The purpose of the prongs is to generate sufficient friction to prevent the plunger from falling out of the barrel but not so much friction that the sliding action of the nasal pack in the barrel is inhibited.

Other related art in the nature of tampon inserting device is shown by U.S. Pat. No. 3,674,026. This patent is directed toward a device having a barrel and a plunger for transporting a tampon pack mounted in the barrel. The tampon has a withdrawal string which exits the rear of the barrel adjacent the outer wall of the plunger. Another tampon inserter having a barrel and a pusher which drives the tampon into a cavity is shown in U.S. Pat. No. 4,291,696. See, also U.S. Pat. Nos. 3,971,378 which shows a fan shaped tampon housed in a barrel which is pushed into the cavity by a plunger member and 636,637 which discloses a gauze carrier having a barrel and plunger used to pack nasal cavities.

SUMMARY OF THE INVENTION

The present invention is directed toward a nasal pack inserter apparatus constructed with a barrel member having a throughgoing lumen providing inlet and outlet openings for a plunger mechanism which is inserted into the lumen. Such a construction is of course required for any tampon applicator. The interior surface of the barrel member defining the lumen also defines inwardly projecting ribs which form a track for the plunger member. The plunger member is constructed to be mounted in the track and is reciprocally moveable in relation thereto. The plunger member is formed with a linear body, a thumb grip mounted on one end of body and a pusher tip secured to the opposite end of the body. The linear body defines a plurality of guide members running longitudinally along the interior surface of body and a channel is formed in the body between the guide members. The longitudinal sides of the body are provided with an end guide member so that the plunger member is configured to slideably fit in the barrel rib track. The pusher tip located on the distal end of the body engages a nasal pack provided with a withdrawal thread and propels the nasal pack forward with the withdrawal thread of the nasal pack being positioned in the channel formed in the plunger member.

It is an additional object of the invention to provide the barrel of the inserter with slits which open into the central lumen so that a lubricating cream may be applied to the barrel aiding in insertion of the nasal inserter into the nasal cavity thus allowing the lubricating cream to be deposited along the sides of the barrel and the nasal cavity as the barrel is inserted up into the nasal cavity.

In the accompanying drawings, there is shown an illustrative embodiment of the invention from which these and other of objectives, novel features and advantages will be readily apparent.

BRIEF DESCRIPTION OF THE DRAWINGS

FIG. 1 is a top plan view of the barrel of the inventive nasal inserter apparatus;

FIG. 2 is a side elevational view of the nasal inserter barrel shown in FIG. 1;

FIG. 3 is a rear elevational view of the nasal inserter barrel shown in FIG. 1;

FIG. 4 is an enlarged cross sectional view taken along line 4'–4' of FIG. 1;

FIG. 5 is a partial cross sectional view taken along line 5'–5' of FIG. 2;

FIG. 6 is a cross sectional view along line 6'–6' of FIG. 1;

FIG. 7 is a side elevational view of the pusher and thumb piece of the present invention;

FIG. 8 is a top plan view of the pusher and thumb piece shown in FIG. 7;

FIG. 9 is a front elevational view of the pusher and thumb piece shown in FIG. 8;

FIG. 10 is a cross sectional view taken along line 10'–10' of FIG. 8;

FIG. 11 is a rear elevational view of the pusher and thumb piece shown in FIG. 8;

FIG. 12 is an enlarged partial view of the pusher head shown in circle 12' of FIG. 8; and FIG. 13 is a perspective view of the nasal pack which is inserted with the applicator.

DETAILED DESCRIPTION OF THE INVENTION

The preferred embodiment and best mode of the invention is shown in FIGS. 1 through 12. The present invention is directed toward a nasal pack applicator apparatus 20 approximately 10 cm long constucted with a barrel 30 and plunger 50. The barrel 30 is shown in FIGS. 1-6 and is formed with a "T" shaped handle 32 secured to a stepped rectangularly shaped tube 34 having a rounded end 36. The rounded tip is bulbous and reduces traumatization of the tissue if inserted in the nasal cavity. The barrel 30 is approximately 0.8 cm in width at its distal end. The handle and tube are formed of molded one piece integral plastic and both portions define a throughgoing lumen 38 which extends from the handle to the distal end of the tube 34. The handle 32 is flanged outward to form finger grip flanges 33. The flanges and handle form a curved "C" shaped cross sectional end defining a recess 35 which holds the thumb grip 52 of the plunger's proximal end on top of the rear surface of the handle when the plunger has been fully inserted into the barrel lumen 38. The handle 32 also is provided with a series of external ribs 37 which run on the opposite sides of the handle to aid in gripping the handle. The inner surface 39 of the handle and inner tube surface defining lumen 38 also defines a number of opposed ribs 44 as best seen in FIG. 4 which guide and hold the plunger 50. The tube 34 defines two throughgoing round bores 40 and 42 in its mid-section which allow visual confirmation of the location of the plunger and associated nasal plug 60 in lumen 38 and a series of opposing spaced slots 46 at its distal end which are staggered with respect to an opposite series of spaced slots on the other side of the tube. An antibiotic dispersion cream such as BACACITRACIN, GENTOMYCIN OR NEOMYCIN commonly available on the market is dispensed into the slots 46 for lubrication of the outer surface of the barrel tube and nasal pack when it passes through the slot area. This lubrication provides for protection of the tissues of the nasal cavity when the applicator is inserted into the nasal cavity and lubricates the nasal pack as it is transported through the barrel into the nasal cavity. In addition the antibiotic dispersion will have the desired antibiotic effect within the nasal cavity.

The plunger 50 is constructed with a thumb grip 52 having a knurled, serrated or ribbed outer surface 54 as shown in FIG. 11 and a linear pusher bar body 56 having central ribs 58 and outer guide bars 60 which are slidably mounted in the lumen 38 in tracks 62 formed outside of the guide ribs adjacent the side walls of the barrel lumen. A string guide channel 59 is cut into or formed in the body of the plunger between central ribs 58 to receive the nasal pack pull string 82. As shown in FIG. 12, the distal end of the pusher bar body 56 is formed with a pusher tip 64 having an undulating frontal surface 65 with forward pack engaging portions 66 and a recessed portion 67. The pusher tip defines an internal void or chamber 69 behind the frontal surface 65. A channel 68 which is axially alligned with string channel 59 is formed in recessed portion 67.

The present nasal pack 80 as shown in FIG. 13 is made of a polyvinyl acetal sponge material described in U.S. Pat. No. 4,098,728 issued Jul. 4, 1978. The nasal pack 80 used in the applicator is 9 cm (about 3.5 inches) in length, 0.58 cm (about ¼ inch) in width and 0.29 cm (about ⅛ inch) in thickness. The pack is dry, packaged sterile and cut to size.

The material used in the nasal pack is Merocel CF50 polyvinyl acetal sponge material, a commercially available material manufactured by the Merocel Corporation. This material has been used for nasal packs. The material is a homogeneous white, open-celled sponge with visible pores, instantaneous fluid wicking, absorptive capacity of up 25 times it weight in fluids, a retained fluid capacity of 16 times its own weight in fluids as measured by ASTM D-1117-80, and a pore size range (diameter) of 0.02 to 1.2 mm as determined by Scanning Electron Microscopy at 10× and 100× magnifications. The nasal pack 80 as seen in FIG. 14 has a generally rectangular configeration with rounded ends and is provided with a end pull string 82 attached to the end of the nasal pack.

In operation the nasal pack 80 is loaded into the lumen 38 of the barrel over ribs 44; plunger 50 is pushed behind the nasal pack and is seated in the tracks 62 formed by the barrel ribs and sides of the lumen. The withdrawal string 82 of the nasal pack 80 is mounted inside the plunger body in channel 59. The tip 36 of the barrel is inserted to the entrance of or just inside the nasal cavity of the patient and the plunger end 56 is moved toward the end of the barrel pushing the nasal pack forward until it is deposited into the nasal cavity. The barrel and plunger is then removed from the nasal cavity, leaving the nasal pack in the nasal cavity with the pull string extending outside of the nasal cavity.

In the foregoing description, the invention has been described with reference to a particular preferred embodiment, although it is to be understood that specific details shown are merely illustrative, and the invention may be carried out in other ways without departing from the true spirit and scope of the following claims:

What is claimed is;

1. A nasal inserter apparatus comprising: a barrel member with a throughgoing lumen providing inlet means and outlet means, said barrel member defining rib means projecting into said throughgoing lumen defining a track means, one end of said barrel member being flanged to form a handle, said flanged end defining a recess to hold a plunger member thumb piece; a plunger member mounted in said lumen of said barrel member and moveable in relation thereto, said plunger member being configured to fit in said track means when inserted in said inlet means of said barrel member and slidable in said track means, said plunger member having a thumb piece on one end and a pusher tip on the other end to transport a nasal pack provided with a withdrawal thread through said lumen into a nasal cavity, said nasal pack being pushed forward by said pusher tip of said plunger member with said withdrawal thread being positioned in said plunger member.

2. An apparatus as claimed in claim 1 wherein said barrel member has a rectangular cross section.

3. An apparatus as claimed in claim 1 wherein said plunger member tip defines a central chamber.

4. An apparatus as claimed in claim 1 wherein said plunger member tip has a front portion with curved end sections and a recessed curved center section.

5. An apparatus as claimed in claim 1 wherein said plunger member tip has a front portion which defines a channel which is axially aligned with said lumen.

6. An apparatus as claimed in claim 1 wherein said plunger member comprises a linear body, a thumb grip mounted on one end of said body and a pusher tip secured to the opposite end of said body, said body defining a plurality of guide members running longitudinally along the surface of said body, a channel formed in said body and an end guide on each side running longitudinally along the surface of said body.

7. An apparatus as claimed in claim 1 wherein said barrel member has a rounded distal tip.

8. An apparatus as claimed in claim 1 wherein said barrel member defines a plurality of slots on opposing sides of said barrel, said slots extending through a side wall of said barrel member into said lumen.

9. An apparatus as claimed in claim 8 wherein said barrel member plurality of slots are staggered with respect to a plurality of slots on the opposite side of said barrel member.

10. A nasal inserter apparatus comprising: a barrel member with a throughgoing lumen providing inlet means and outlet means, said barrel member defining rib means projecting into said throughgoing lumen to form a track means, one end of said barrel member provided with handle means, said handle means having a substantially C shaped cross section to receive a thumb grip of a plunger member; a plunger member mounted in said lumen of said barrel member and moveable in relation thereto, said plunger member being configured to fit in said track means when inserted in said inlet means of said barrel member and slidable in said track means, said plunger member comprising a linear body, a thumb grip mounted on one end of said body and a pusher tip secured to the opposite end of said body, said linear body defining a plurality of guide members running longitudinally along the surface of said body, a channel formed in said body between said guide members and a side guide rail member formed on each side of said body, said pusher tip on the other end engaging a nasal pack provided with a withdrawal thread, said nasal pack being pushed forward by a tip of said plunger member with said withdrawal thread being positioned in a channel formed in said plunger member.

11. An apparatus as claimed in claim 10 wherein said plunger member distal tip has two curved front sections which intersect in a central portion which defines a tip channel, said tip channel being axially aligned with said plunger body channel.

12. An apparatus as claimed in claim 10 wherein said plunger member distal tip defines a central throughgoing chamber.

13. An apparatus as claimed in claim 10 wherein said barrel member has a rounded distal end.

14. An apparatus as claimed in claim 10 wherein said barrel member has a rectangular shape with at least two opposing sides of said barrel member defining a plurality of slots, said slots extending through a side wall of said barrel member into said lumen.

15. An apparatus as claimed in claim 14 wherein said barrel member plurality of slots are staggered with respect to the plurality of slots on the opposite side of said barrel member.

16. A nasal inserter apparatus comprising: a barrel member with a distal rounded bulbous tip and a throughgoing lumen providing inlet means and outlet means, said barrel member defining both rib means projecting into said throughgoing lumen defining a track means and a plurality of slots on opposing sides of said barrel, said slots extending through the side wall of said barrel member into said lumen, a plunger member mounted in said lumen of said barrel member and moveable in relation thereto, said plunger member being configured to fit in said track means when inserted in said inlet means of said barrel member and slidable in said track means, said plunger member having a thumb piece on one end and a pusher tip on the other end to transport a nasal pack provided with a withdrawal thread through said lumen into a nasal cavity, said pusher tip defining a curved recessed central portion with projecting curved side portions which engage said nasal pack, said pusher tip also defining a central chamber, said nasal pack being pushed forward by a tip of said plunger member with said withdrawal thread being positioned in said plunger member.

* * * * *